US005932429A

United States Patent [19]
Targan et al.

[11] Patent Number: 5,932,429
[45] Date of Patent: Aug. 3, 1999

[54] METHODS OF DIAGNOSING CLINICAL SUBTYPES OF CROHN'S DISEASE

[75] Inventors: Stephan R. Targan, Santa Monica; Eric A. Vasiliauskas, Hermosa Beach, both of Calif.; Scott E. Plevy, Tenafly, N.J.; Mary J. Barry, Ramona, Calif.

[73] Assignees: Cedars-Sinai Medical Center, Los Angeles; Prometheus Laboratories Inc., San Diego, both of Calif.

[21] Appl. No.: 08/837,059

[22] Filed: Apr. 11, 1997

Related U.S. Application Data

[63] Continuation-in-part of application No. 08/630,672, Apr. 12, 1996, abandoned.

[51] Int. Cl.$^6$ .................................................. G01N 33/564
[52] U.S. Cl. ...................... 435/7.24; 435/7.31; 435/7.95; 435/975; 436/506; 436/508
[58] Field of Search .................................. 435/7.24, 7.31, 435/7.95, 975; 436/506, 508

[56] References Cited

PUBLICATIONS

Quinton et al, Gastroenterology, 112(4), A 1066, 1997.
Vasiliauskas et al, Gastroenterology, 112(4), A 1112, 1997.
Barnes et al., "Serum Antibodies Reactive with *Saccharomyces cerevisiae* in Inflammatory Bowel Disease: Is IgA Antibody a Marker for Crohn's Disease?," *Int. Arch. Allergy Appl. Immunol.* 92:9–15 (1990).
Broekroelofs et al., "Anti–Neutrophil Cytoplasmic Antibodies (ANCA) in Sera from Patients with Inflammatory Bowel Disease (IBD) ," *Dig. Dis. Sci.* 39:545–549 (1994).
Cambridge et al., "Anti–neutrophil Antibodies in Inflammatory Bowel Disease: Prevalence and Diagnostic Role," *Gut* 33:668–674 (1992).
Duerr et al., "Anti–neutrophil Cytoplasmic Antibodies in Ulcerative Colitis," *Gastroenterol.* 100:1590–1596 (1991).
Faille et al., "Evaluation of an Enzyme Immunoassay Using Neoglycolipids Constructed from *Candida* albicans Oligomannosides to Define the Specificity of Anti–Mannan Antibodies," *Eur. J. Clin. Microbiol. Infect. Dis.* 11:438–446 (1992).
Giaffer et al., "Antibodies to *Saccharomyces cerevisiae* in Patients with Crohn's Disease and Their Possible Pathogenic Importance," *Gut* 33:1071–1075 (1992).
Hardarson et al., "Antineutrophil Cytoplasmic Antibody in Inflammatory Bowel and Hepatobiliary Diseases," *Amer. J. Clin. Pathol.* 99:277–281 (1993).
Lennard–Jones, "Classification of Inflammatory Bowel Disease," *Scand. J. Gastroenterol. Suppl.* 24:2–6, 16–19 (1989).
Lindberg et al., "Antibody (IgG, IgA, and IgM) to Baker's Yeast (*Saccharomyces cerevisiae*), Yeast Mannan, Giadin, Ovalbumin and Betalactoglobulin in Monozygotic Twins with Inflammatory Bowel Disease," *Gut* 33:909–913 (1992).

Main et al., "Antibody to *Sacharomyces cerevisiae* (baker's yeast) in Crohn's Disease," *British Medical Journal* 297:1105–1106 (1988).
McKenzie et al., "Antibody to Selected Strains of *Saccharomyces cerevisiae* (baker's and brewer's yeast) and *Candida albicans* an Crohn's Disease," *Gut* 31:536–538 (1990).
McKenzie et al., "Antigenic Heterogeneity of Strains of *Saccharomyces cerevisiae* and *Candida albicans* Recognized by Serum Antibodies from Patients with Crohn's Disease," *FEMS Microbiology Immunology* 89:219–224 (1992).
Orholm et al., "Familial Occurrence of Inflammatory Bowel Disease," *N. Engl. J. Med.* 324:84–88 (1991).
Patel et al., "Influence of Total Colectomy on Serum Antineutrophil Cytoplasmic Antibodies in Inflammatory Bowel Disease," *Brit. J. Surg.* 81:724–726 (1994).
Pool et al., "Serum Antineutrophil Cytoplasmic Autoantibodies in Inflammatory Bowel Disease are Mainly Associated with Ulcerative Colitis. A Correlation Study Between Perinuclear Antineutrophil Cytoplasmic Autoantibodies and Clinical Parameters, Medical, and Surgical Treatment," *Gut* 34:46–50 (1993).
Price, "Overlap in the Spectrum of Non–Specific Inflammatory Bowel Disease–'Colitis Indeterminate,'" *J. Clin. Pathol.* 31:567–577 (1978).

(List continued on next page.)

*Primary Examiner*—David Saunders
*Attorney, Agent, or Firm*—Campbell & Flores

[57] ABSTRACT

Provided herein is a method of diagnosing a clinical subtype of Crohn's disease (CD) by determining whether perinuclear anti-neutrophil antibody (pANCA) is present in a patient with CD, where the presence of pANCA indicates a clinical subtype of CD with features of ulcerative colitis (UC). Also provided is a method of diagnosing a clinical subtype of Crohn's disease in a patient with CD by determining whether pANCA or speckling anti-pan polymorphonuclear antibody (SAPPA) is present in the patient with CD, where the presence of pANCA indicates a clinical subtype of CD with features of ulcerative colitis and where the presence of SAPPA indicates a clinical subtype of CD having perforating, fistulizing or small bowel obstructive disease. The invention further provides a method of diagnosing a clinical subtype of Crohn's disease in a patient with CD by determining the presence or absence of ANCA, pANCA, SAPPA and anti-*Saccharomyces cerevisiae* antibodies (ASCA) in the patient with CD, where the presence of pANCA combined with the absence of ASCA indicate a clinical subtype of CD with features of UC, the presence of SAPPA indicates a clinical subtype of CD having perforating or fistulizing disease or small bowel obstructive disease, and the presence of ASCA combined with the absence of ANCA indicates a clinical subtype of CD lacking features of ulcerative colitis and having perforating or fistulizing disease or small bowel obstructive disease. Kits for diagnosing a clinical subtype of Crohn's disease, which contain neutrophil and antigen specific for ASCA, also are provided.

32 Claims, 4 Drawing Sheets

OTHER PUBLICATIONS

Proujansky et al., "Examination of Anti–neutrophil Cytoplasmic Antibodies in Childhood Inflammatory Bowel Disease," *J. Pediatr. Gastroenterol. and Nutr.* 17:193–197 (1993).

Rubin and Farber (eds.), "Inflammatory Bowel Disease," *Pathology* (2nd Ed.), pp. 675–683 (1994).

Saxon et al., "A Distinct Subset of Antineutrophil Cytoplasmic Antibodies is Associated with Inflammatory Bowel Disease," *J. Allergy Clin. Immunol.* 86:202–210 (1990).

Schacter and Kirsner, "Definitions of Inflammatory Bowel Disease of Unknown Etiology," *Gastroenterol.* 68:591–600 (1975).

Sendid et al., "Specific Antibody Response to Oligomannosidic Epitopes in Crohn's Disease," *Clinical and Diagnostic Laboratory Immunology* 3:219–226 (1996).

Sung et al., "Anti–Neutrophil Cytoplasmic Antibodies (ANCA) and Inflammatory Bowel Diseases in Chinese," *Dig. Dis. and Sci.* 39:886–892 (1994).

Targan and Murphy, "Clarifying the Causes of Crohn's," *Nature Med.* 1:1241–1243 (1995).

Vasiliauskas et al., "Perinuclear Antineutrophil Cytoplasmic Antibodies (pANCA) in Patients with Crohn's Disease (CD) Define a Clinical Subgroup," *Gastroenterol.* 108:A935 (1995).

Vasiliauskas et al., "Perinuclear Antineutrophil Cytoplasmic Antibodies in Patients with Crohn's Disease Define a Clinical Subgroup," *Gastroenterol.* 110:1810–19 (1996).

Young et al., "Lymphocyte Proliferation Response to Baker's Yeast in Crohn's Disease," *Digestion* 55:40–43 (1994).

METHODS OF DIAGNOSING CLINICAL SUBTYPES OF CROHN'S DISEASE

RELATED APPLICATIONS

This application is a continuation-in-part of application Ser. No. 08/630,672, filed Apr. 12, 1996 and now abandoned.

ACKNOWLEDGMENT

This work was supported by USPHS grant DK46763 awarded by The United States Public Health Service. The United States government has certain rights in this invention.

BACKGROUND OF THE INVENTION

1. Field of the Invention

The invention relates generally to the fields of autoimmunity and inflammatory bowel disease and more specifically to serological and genetic methods for diagnosing a clinical subtype of Crohn's disease.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe and in ulcerative colitis often is accompanied by bleeding. Anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Progress has been made in diagnosing IBD and in distinguishing, in many cases, Crohn's disease from ulcerative colitis. However, CD and UC each can represent a number of distinct disease subtypes that affect the gastrointestinal tract and produce similar symptoms. The heterogeneity underlying CD, for example, can be reflected in the variable responses of CD patients to a particular treatment strategy. The availability of methods for diagnosing clinical subtypes of CD would represent a major clinical advance that would aid in the therapeutic management of CD and would provide a basis for the design of treatment modalities that are specific to a particular disease subtype. Unfortunately, a method of stratifying CD into clinical subtypes to allow the design of more precise treatment strategies is currently not available. Thus, there is a need for a method of diagnosing clinical subtypes of CD. The present invention satisfies this need and provides related advantages as well.

SUMMARY OF THE INVENTION

The present invention provides a method of diagnosing a clinical subtype of Crohn's disease (CD) by determining whether perinuclear anti-neutrophil antibody (pANCA) is present in a patient with CD, where the presence of pANCA indicates a clinical subtype of CD with features of ulcerative colitis (UC). Such a clinical subtype can be diagnosed, for example, by obtaining a serum sample from a patient with CD; determining whether anti-neutrophil cytoplasmic antibody (ANCA) is detectable in patient sera diluted at least about 100-fold; and assaying for the presence or absence of a pANCA staining pattern, where detection of ANCA in patient sera diluted at least about 100-fold and the presence of a pANCA staining pattern indicate the presence of pANCA, provided that detection of ANCA is not by histological methods.

The present invention also provides a method of diagnosing clinical subtypes of Crohn's disease in a patient with CD by determining whether pANCA or SAPPA is present in the patient with CD, where the presence of pANCA indicates a clinical subtype of CD with features of ulcerative colitis and where the presence of SAPPA indicates a clinical subtype of CD having perforating, fistulizing or small bowel obstructive disease.

The invention further provides a method of diagnosing clinical subtypes of Crohn's disease in a patient with CD by determining the presence or absence of ANCA, pANCA and SAPPA in the patient with CD and determining the presence or absence of anti-*Saccharomyces cerevisiae* antibodies (ASCA) in the patient with CD, where the presence of pANCA and the absence of ASCA indicate a clinical subtype of CD with features of UC, the presence of SAPPA indicates a clinical subtype of CD having perforating, fistulizing or small bowel obstructive disease, and the presence of ASCA and the absence of ANCA indicates a clinical subtype of CD lacking features of ulcerative colitis and having perforating, fistulizing or small bowel obstructive disease.

Kits for diagnosing clinical subtypes of Crohn's disease, which contain neutrophil and antigen specific for ASCA, also are provided. Kits of the invention can include, for example, neutrophil and yeast cell wall phosphopeptidomannan. If desired, one or more secondary antibodies selective for ASCA or one or more secondary antibodies selective for ANCA also can be included.

DETAILED DESCRIPTION OF THE INVENTION

Figure 1:
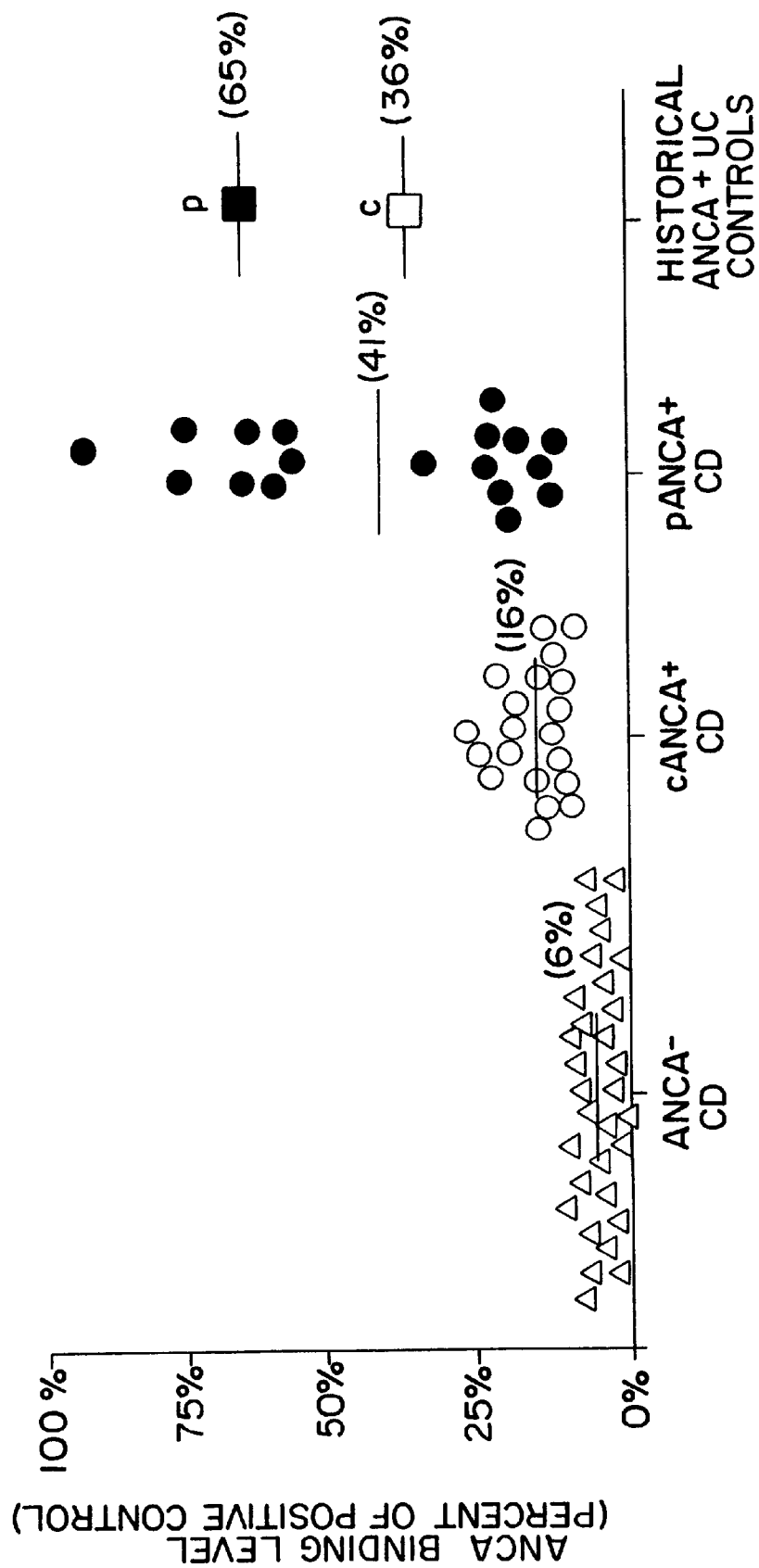
FIG. 1 shows the inflammatory disease-associated ANCA in sera from Crohn's disease patients analyzed by indirect immunofluorescence and by ELISA, with results expressed as percent of positive control. The solid line in each column represents the mean binding. respectively.

Although Crohn's disease (CD) and ulcerative colitis (UC) generally have been considered distinct diseases, the present invention is directed to the surprising discovery that there is a clinical subtype of CD patients that also have features of UC. The invention provides convenient, non-invasive serological assays for diagnosing this clinical subtype.

The invention provides a method of diagnosing a clinical subtype of Crohn's disease by determining whether pANCA is present in a patient with CD, where the presence of pANCA indicates a clinical subtype of CD with features of ulcerative colitis.

As disclosed herein, the presence of pANCA in a Crohn's disease patient indicates a clinical subtype of CD, which is characterized by features of ulcerative colitis in addition to the features that are typical of CD. As described in Example IA, the presence of pANCA was determined in a group of 69 CD patients, where pANCA was determined to be present if ANCA was detectable in patient sera diluted 100-fold using a fixed neutrophil enzyme-linked immunosorbent assay (ELISA) and if a pANCA staining pattern was present as determined by indirect immunofluorescence using fixed neutrophil. Using these criteria to establish whether pANCA was present in a patient with CD, 100% percent of CD patients in which pANCA was present exhibited features of ulcerative colitis (see Example IB). The frequency of features of ulcerative colitis in the pANCA-positive CD subgroup was significantly higher than the frequency of features of ulcerative colitis in the cANCA-positive subgroup (45%) or the ANCA-negative CD subgroup (39%). Although Crohn's disease and ulcerative colitis generally have been considered to be distinct disorders, these results demonstrate that a subtype of patients having disease characterized by features of both UC and CD, can be diagnosed by the presence of pANCA.

The methods of the invention for diagnosing a clinical subtype of CD with features of ulcerative colitis are useful for the medical management of this subtype of Crohn's patients. The heterogeneity underlying Crohn's disease generally is reflected in variable responses of CD patients to a given treatment strategy. However, pANCA-positive CD patients suffer from a similar type of mucosal inflammation and respond similarly to a particular course of therapy. Furthermore, therapeutic strategies that are efficacious in the management of UC also can be used to treat the clinical subtype of CD with features of UC, while other Crohn's disease patients are unresponsive. For example, colectomy to remove diseased colonic mucosa with creation of an ileal pouch to preserve continence is frequently recommended for uncontrolled UC. While the general population of Crohn's disease patients typically cannot tolerate a pouch, such surgery can be a viable option for the subtype of CD patients whose disease is characterized by features of UC. Other therapeutic strategies, such as anti-tumor necrosis factor-α (TNF-α) inflammatories, for example, can best be used to treat Crohn's disease patients that are not pANCA-positive. Thus, the methods of the invention are useful for the differential diagnosis, treatment and medical management of patients having CD.

Inflammatory bowel disease has been classified into the broad categories of Crohn's disease and ulcerative colitis. Crohn's disease (regional enteritis) is a disease of chronic inflammation that can involve any part of the gastrointestinal tract. Commonly the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also includes complications such as inflammation of the eye, joints and skin; liver disease; kidney stones or amyloidosis. In addition, CD is associated with an increased risk of intestinal cancer.

Several features are characteristic of the pathology of Crohn's disease. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. About half of Crohn's disease cases display the typical discrete granulomas, while others show a diffuse granulomatous reaction or nonspecific transmural inflammation. As a result, the presence of discrete granulomas is indicative of CD, although the absence granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J.B. Lippincott Company (1994), which is incorporated herein by reference).

Ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, supra, 1994).

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers or fistulas suggest Crohn's disease. Characteristics that serve to distinguish Crohn's disease from ulcerative colitis are summarized in Table 1 (Rubin and Farber, supra, 1994).

As used herein, the term "patient with Crohn's disease" is synonymous with "patient with CD" and means a patient having a characteristic feature from at least two of the following categories: clinical, endoscopic, radiographic and histopathologic. As used herein, a characteristic clinical feature is perforating or fistulizing disease; or an obstructive symptom secondary to small bowel stenosis or stricture. As used herein, a characteristic endoscopic feature is a deep linear or serpiginous ulceration; a discrete ulcer in normal-appearing mucosa; cobblestoning; or discontinuous or asymmetric inflammation. As used herein, a characteristic radiographic feature is segmental disease (skip lesion); a small bowel or colon stricture; stenosis or fistula. As used herein, a characteristic histopathologic feature is submucosal or transmural inflammation; multiple granulomas; marked focal cryptitis or focal chronic inflammatory infiltration within and between biopsies; or a skip lesion, including histologic rectal sparing in the absence of local therapy.

TABLE 1

Characteristic Features of Crohn's disease and ulcerative colitis

| Feature | Crohn's Disease | Ulcerative Colitis |
| --- | --- | --- |
| Macroscopic | | |
| Thickened bowel wall | Typical | Uncommon |
| Luminal narrowing | Typical | Uncommon |
| "Skip" lesions | Common | Absent |
| Right colon predominance | Typical | Absent |
| Fissures and fistulas | Common | Absent |
| Circumscribed ulcers | Common | Absent |
| Confluent linear ulcers | Common | Absent |
| Pseudopolyps | Absent | Common |
| Microscopic | | |
| Transmural inflammation | Typical | Uncommon |
| Submucosal fibrosis | Typical | Absent |
| Fissures | Typical | Rare |
| Granulomas | Common | Absent |
| Crypt abscesses | Uncommon | Typical |

As used herein, the term "features of ulcerative colitis" or "features of UC" means clinical features of left-sided colonic disease accompanied by a characteristic endoscopic or histopathologic feature of UC. Clinical features of left-sided colonic disease, as used herein, are rectal

TABLE 2

Characteristic Clinical, Endoscopic and Histopathologic Features of Ulcerative Colitis

| A. Clinical features of left-sided colonic disease | 1. Rectal bleeding possibly accompanied by mucus discharge<br>2. Urgency<br>3. Tenesmus<br>4. Treatment with topical therapy<br>5. Recommended or performed total or near-total colectomy |
| --- | --- |

TABLE 2-continued

Characteristic Clinical, Endoscopic and Histopathologic Features of Ulcerative Colitis

| B. Endoscopic features of UC | 6. Inflammation that is more severe distally than proximally<br>7. Continuous inflammation<br>8. Inflammation extending proximally from the rectum<br>9. Shallow ulcerations or lack of deep ulcerations |
| --- | --- |
| C. Histopathologic features of UC | 10. Homogeneous, continuous, predominantly superficial inflammation<br>11. Lack of "focality" within biopsy specimens<br>12. Crypt abscesses<br>13. Lack of granulomas | bleeding, urgency and tenesmus. The rectal bleeding can be accompanied by mucus discharge. An additional typical clinical feature can be treatment with topical therapy or recommended or performed total or near-total colectomy. A characteristic endoscopic feature of UC, which when present with clinical features of left-sided colonic disease indicates features of ulcerative colitis, is inflammation that is more severe distally than proximally or continuous inflammation. An additional typical endoscopic feature can be inflammation extending proximally from the rectum or shallow ulcerations or the lack of deep ulcerations. A characteristic histopathologic feature of UC, which when present with clinical features of left-sided colonic disease indicates features of ulcerative colitis, is homogeneous, continuous, predominantly superficial inflammation or a lack of "focality" within biopsy specimens. An additional typical histopathologic feature can be a crypt abscess or the lack of granulomas. Characteristic clinical, endoscopic and histopathologic features of ulcerative colitis are summarized in Table 2.

Patients with chronic inflammatory bowel disease generally are characterized as having either Crohn's disease or ulcerative colitis to describe specific patterns of disease, to predict outcomes based on expected natural histories, and to help guide medical and surgical treatment strategies. Clinical, endoscopic, and histopathologic criteria, as discussed above, have been developed to classify patients into one or the other category. However, overlap between CD and UC also has been demonstrated at a variety of levels by clinical, immunological and genetic studies, for example. Furthermore, CD and UC each can encompass a number of distinct conditions affecting the gastrointestinal tract, with different clinical subtypes being classified together as CD or UC because they present with similar symptoms. The present invention is directed to the discovery that such a clinical subtype, in particular a clinical subtype of CD with features of ulcerative colitis, can be diagnosed using perinuclear anti-neutrophil cytoplasmic antibodies (pANCA).

In another embodiment, the invention provides a method of diagnosing clinical subtypes of Crohn's disease in a patient with CD by determining whether pANCA or speckling anti-pan polymorphonuclear antibody (SAPPA) is present in the patient with CD, where the presence of pANCA indicates a clinical subtype of CD with features of ulcerative colitis and where the presence of SAPPA indicates a clinical subtype of CD having perforating, fistulizing or small bowel obstructive disease.

The methods of the invention for diagnosing clinical subtypes of Crohn's disease involve determining whether pANCA or SAPPA is present in a patient having CD. Such serum antibodies to cytoplasmic components of a neutrophil (ANCA) can be detected, for example, using indirect immunofluorescence microscopy of alcohol-fixed neutrophils. As disclosed herein, ANCA activity is divided into several broad categories: perinuclear to nuclear staining or cytoplasmic staining with perinuclear highlighting (pANCA); diffuse staining with speckling across the entire neutrophil (SAPPA); and cytoplasmic neutrophil staining without perinuclear highlighting (cANCA). The term "anti-neutrophil cytoplasmic antibody" is synonymous with "ANCA" and encompasses pANCA, SAPPA and cANCA.

As used herein, the term "ANCA" encompasses pANCA, SAPPA and cANCA. Similarly, the term "ANCA-positivity" means the presence of ANCA, whether pANCA, SAPPA or cANCA. The term "low level ANCA-positivity" means a level of ANCA-positivity less than about 40% of the level of ANCA-positivity of well characterized pANCA-positive UC sera.

As used herein, the term "perinuclear anti-neutrophil cytoplasmic antibody" is synonymous with "pANCA" and refers to an antibody that reacts specifically with a neutrophil to give perinuclear to nuclear staining or cytoplasmic staining with perinuclear highlighting. The term "pANCA-positive," when used in reference to a patient, means a patient having pANCA. The term "pANCA staining pattern" means a perinuclear to nuclear staining pattern or a cytoplasmic staining pattern with perinuclear highlighting that distinguishes pANCA from, for example, SAPPA and cANCA. The pANCA staining pattern is shown in panel (b) of FIG. 4.

As used herein, the term "speckling anti-pan polymorphonuclear antibody" is synonymous with "SAPPA" and refers to an anti-neutrophil antibody that gives low level ANCA-positivity and that reacts specifically with a neutrophil to give diffuse staining with speckling across the entire cell. The term "SAPPA-positive," when used in reference to a patient, means a patient having SAPPA. The term "SAPPA staining pattern" means a diffuse staining pattern with speckling across the entire surface of a neutrophil that distinguishes SAPPA from, for example, pANCA and cANCA. The SAPPA staining pattern is shown in panel (c) of FIG. 4.

Anti-neutrophil cytoplasmic antibodies that produce a perinuclear staining pattern are elevated in 68–80% of UC patients and less frequently in CD and other disorders of the colon. Serum titers of ANCA are elevated regardless of clinical status and, thus, do not reflect disease activity. High levels of serum ANCA also persist in patients five years post-colectomy. Although pANCA is found only very rarely in healthy adults and children, healthy relatives of UC patients have an increased frequency of pANCA, indicating that pANCA may be an immunogenetic susceptibility marker.

Previous studies have also shown ANCA reactivity in a small portion of patients with Crohn's disease although these antibodies are elevated more frequently in patients with ulcerative colitis. The reported prevalence in CD varies from 0 to 43% with most studies reporting that 10 to 30% of CD patients express ANCA (see, for example, Saxon et al., *J. Allergy Clin. Immunol*. 86:202–210 (1990); Cambridge et al., *Gut* 33:668–674 (1992); Pool et al., *Gut* 3446–50 (1993); and Brokroelofs et al., *Dig. Dis. Sci*. 39:545–549 (1994).

The pANCA-positive subtype of Crohn's disease does not correlate with traditional CD subgroups based on, for example, location of disease (small bowel only, colon only, or small bowel and colon); extent of disease; duration of illness; disease activity; medical therapy; or surgical history (Cambridge et al., supra, 1992; Pool et al., supra, 1993; Brokroelofs et al., supra, 1994). Previous work has suggested that ANCA expression in CD patients may be related to colonic disease (Sung et al., *Dig. Dis. Sci*. 39:886–892 (1994); Proujansky et al., *J. Pediatr. Gastroenterol. Nutr*. 17:193–197 (1993); and Patel et al., *Br. J. Surg*. 81:724–726 (1994)). However, the majority of CD patients with colonic disease are not pANCA-positive, and the presence of colonic disease alone does not characterize the pANCA-positive subtype of CD patients. As disclosed herein, the presence of pANCA in CD is instead diagnostic of features of ulcerative colitis such as left-sided colonic disease in which the distal portion of the colon is more severely inflamed than the proximal portion and clinical symptoms of left-sided colonic inflammation such as rectal bleeding.

In the methods of the invention, the presence of pANCA or the presence of SAPPA can be determined as described in Example III. The presence of pANCA or the presence of SAPPA can be determined using a sample obtained from any biological fluid having ANCA such as, for example, whole blood, plasma or other bodily fluid or tissue having ANCA, preferably serum. When multiple samples are used in an assay for determining the presence of pANCA or SAPPA, it is preferred that the same type of biological fluid or tissue is used for each sample.

A serum sample diluted at least about 100-fold is particularly usefull in the methods of the invention. For example, the invention provides a method of diagnosing a clinical subtype of Crohn's disease by determining whether pANCA is present in a patient with CD can be practiced by obtaining a serum sample from the patient with CD; determining whether anti-neutrophil cytoplasmic antibody (ANCA) is detectable in patient sera diluted at least about 100-fold; and assaying for the presence or absence of a pANCA staining pattern, where detection of ANCA in patient sera diluted at least about 100-fold and the presence of a pANCA staining pattern indicate the presence of pANCA, if the detection of ANCA is not by histological means.

The invention also provides a method of diagnosing clinical subtypes of Crohn's disease in a patient with CD by determining whether pANCA or SAPPA is present in the patient with CD by obtaining a serum sample from said patient with CD, determining by non-histological means the level of ANCA-positivity in patient sera diluted at least about 100-fold, and assaying for the presence or absence of a pANCA or SAPPA staining pattern, where detection of ANCA in patient sera diluted at least about 100-fold and the presence of a pANCA staining pattern indicate the presence of pANCA and where the detection of low level ANCA-positivity in patient sera diluted at least about 100-fold and the presence of a SAPPA staining pattern indicate the presence of SAPPA, provided that said detection of ANCA is not by histological means.

Numerous studies have used indirect immunofluorescence alone to detect the presence of serum ANCA, thereby determining whether pANCA is present simply on the basis of a pANCA staining pattern. Furthermore, where a quantitative assay has been relied upon in addition to a staining pattern, detection of ANCA has been determined using a relatively high concentration of patient sera, such as a 20-fold or 40-fold dilution of sera, for example. In contrast, the present invention is directed to the discovery that the presence of pANCA or SAPPA, as determined rigorously by both analyzing the level of ANCA reactivity in patient sera diluted at least about 100-fold and the presence of a pANCA or SAPPA staining pattern, is diagnostic of particular clinical subtypes of CD, provided that detection of ANCA in patient sera is not by histological means.

As used herein, the term "histological means," when used in reference to detection of ANCA or detection of a first complex of antigen and ANCA as described below, refers to a technique for studying the structure of a cell or tissue using staining and microscopy. Histological means, which encompass techniques such as immunocytochemistry and indirect immunofluorescence, can distinguish pANCA, SAPPA and cANCA staining patterns and, thus, are useful in assaying for the presence or absence of a pANCA or SAPPA staining pattern, for example. However, histological means, which typically are subjective, are not useful for rigorously determining whether ANCA is detectable in patient sera diluted at least about 100-fold or determining the level of ANCA-positivity. The use of histology, as defined herein, for determining whether ANCA is detectable in patient sera diluted at least about 100-fold ,or the level of ANCA-positivity in patient sera diluted at least about 100-fold, is explicitly excluded from the present invention. Similarly, the present invention explicitly excludes the use of histological means to detect the presence or absence of a first complex of antigen and ANCA, as described further below.

It is recognized that determining whether ANCA is detectable in patient sera diluted at least about 100-fold can be performed prior to, following or concurrent with assaying for the presence or absence of a pANCA or SAPPA staining pattern. Thus, for example, an immunofluorescence assay for the presence of a pANCA staining pattern followed by an enzyme-linked immunosorbent assay for determining whether ANCA is detectable in patient sera diluted at least about 100-fold is encompassed within the methods of the invention. Similarly, an immunofluorescence assay for the presence of a SAPPA staining pattern followed by an enzyme-linked immunosorbent assay for determining the level of ANCA-positivity in patent sera diluted at least about 100-fold is encompassed within the methods of the invention.

Methods of determining whether ANCA is detectable in patient sera diluted at least about 100-fold, or the level of ANCA-positivity in patient sera diluted at least about 100-fold, are well known in the art (Harlow and Lane, *Antibodies: A Laboratory Manual* New York: Cold Spring Harbor Laboratory (1988), which is incorporated herein by reference). For example, ANCA can be detected in patient sera using a detectable reagent such as a secondary antibody labeled with a detectable enzymatic, radioisotopic, fluorescent or chemiluminescent marker. Particularly useful methods include a quantitative assay such as an immunoassay, in which an antibody selective for ANCA is used to detect ANCA in patient sera and to determine, if desired, the level of ANCA-positivity. A radioimmunoassay (RIA) or enzyme-linked immunosorbent assay (ELISA), for example, is encompassed within the invention. As discussed above, the present invention explicitly excludes the use of histological means such as immunocytochemistry or immunofluorescence for determining whether ANCA is present in patient sera diluted at least about 100-fold and for determining the level of ANCA-positivity in patient sera diluted at least about 100-fold.

An enzyme-linked immunosorbent assay (ELISA) can be useful in determining whether ANCA is present in patient sera diluted at least about 100-fold. For example, a fixed neutrophil ELISA for detection of ANCA in patient sera diluted 100-fold is described in Example III. An enzyme that is linked to a secondary antibody selective for ANCA can be, for example, horseradish peroxidase (HRP), alkaline phosphatase (AP), β-galactosidase or urease. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm, or a urease detection system can be used with a substrate such as urea-bromocresol purple (Sigma Immunochemicals, St. Louis, Mo.). A secondary antibody linked to an enzyme is a detectable reagent useful in an ELISA and can be obtained from a number of commercial sources. For example, goat F(ab')2 anti-human IgG-alkaline phosphatase can be purchased from Jackson Immuno-Research (West Grove, Pa.).

A radioimmunoassay also can be useful in determining whether ANCA is present in patient sera diluted at least about 100-fold and the level of ANCA-positivity in patient sera diluted at least about 100-fold. A radioimmunoassay using, for example, an iodine-125 labeled secondary antibody (Harlow and Lane, supra, 1988) is encompassed within the invention.

A secondary antibody labeled with a chemiluminescent marker also can be useful for determining whether ANCA is present in patient sera diluted at least about 100-fold and for determining the level of ANCA-positivity in patient sera diluted at least about 100-fold. Such a chemiluminescent secondary antibody is convenient for sensitive, non-radioactive detection of ANCA and can be obtained commercially from various sources such as Amersham Lifesciences, Inc. (Arlington Heights, Ill.).

In addition, a detectable reagent labeled with a fluorochrome can be useful in determining whether ANCA is present in patient sera diluted at least about 100-fold or the level of ANCA-positivity in patient sera diluted at least about 100-fold. Appropriate fluorochromes include, for example, DAPI, fluorescein, Hoechst 33258, R-phycocyanin, B-phycoerythrin, R-phycoerythrin, rhodamine, Texas red or lissamine. A particularly useful fluorochrome is fluorescein or rhodamine. A secondary antibody linked to a fluorochrome is a particularly useful detectable reagent and can be obtained commercially. For example, goat F(ab')2 anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of iodine-125; or a fluorometer to detect fluorescence in the presence of light of a certain wavelength. For detection of enzyme-linked reagents, a quantitative analysis of the amount of ANCA can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Immunoassays using a secondary antibody selective for ANCA are particularly useful in the methods of the invention. As used herein, the term "antibody" means a population of immunoglobulin molecules, which can be polyclonal or monoclonal and of any isotype. As used herein, the term antibody encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

As used herein, the term "secondary antibody selective for ANCA" means an antibody, or combination of antibodies, which binds ANCA. Preferably, such a secondary antibody does not compete with neutrophil for binding to ANCA. A secondary antibody can be an anti-ANCA antibody that binds any epitope of ANCA. A particularly useful secondary antibody is an anti-IgG antibody having specificity for the class determining portion of ANCA. A useful secondary antibody is specific for the species of the ANCA to be detected. For example, if human serum is the sample to be assayed, mouse anti-human IgG can be a useful secondary antibody. A combination of different antibodies, which can be useful in the methods of the invention, also is encompassed within the meaning of the term secondary antibody, provided that at least one antibody of the combination binds ANCA.

A secondary antibody useful in an immunoassay of the invention can be obtained commercially or by techniques well known in the art. Such an antibody can be a polyclonal or, preferably, monoclonal antibody that binds ANCA selectively. For example, IgG reactive polyclonal antibodies can be prepared using IgG or Fc fragments of IgG as an immunogen to stimulate the production of antibodies in the antisera of an animal such as a rabbit, goat, sheep or rodent, for example (Harlow and Lane, supra, 1988).

A monoclonal antibody useful in the practice of the invention can be obtained from a number of commercially available sources. In addition, an immunogen useful to generate a monoclonal antibody that binds ANCA selectively can be, for example, human IgG or a Fc fragment of human IgG, ANCA or a Fab fragment of ANCA. A hybridoma that produces a monoclonal selective for ANCA can be identified by screening hybridoma supernatants for the presence of antibodies that bind ANCA specifically (Harlow, supra, 1988). For example, such a screening method can be a radioimmunoassay or enzyme-linked immunosorbent assay using neutrophil and pANCA-positive sera, for example.

Methods of assaying for the presence or absence of a pANCA staining pattern or a SAPPA staining pattern also are well known in the art and are set forth in Example III. Methods of cell staining using, for example, neutrophil, are useful for determining the subcellular localization of ANCA reactivity, thereby differentiating pANCA from SAPPA and cANCA. Immunocytochemistry or immunofluorescence are particularly useful for assaying for the presence of a pANCA staining pattern or a SAPPA staining pattern (Harlow and Lane, supra, 1988). An enzyme-labeled or fluorochrome labeled secondary antibody that binds ANCA selectively, such as described above, can be useful in such methods. For example, indirect immunofluorescence readily can be performed by incubating methanol-fixed neutrophil with a 1:20 dilution of human sera and detecting the complex formed with fluorescein-labeled F(ab')2 γ chain secondary antibody. The presence of the pANCA or SAPPA staining pattern in the stained neutrophils can be visualized using fluorescence microscopy as described in Saxon et al., supra, 1990, or in Example III.

In one embodiment, the invention provides a method of diagnosing a clinical subtype of CD having features of ulcerative colitis by determining whether pANCA is present in a patient with CD by obtaining a serum sample from the patient with CD; contacting the serum sample diluted at least about 100-fold with antigen specific for ANCA under conditions suitable to form a first complex of antigen and ANCA; detecting the presence or absence of the first complex; contacting an appropriate dilution of the serum sample with antigen specific for ANCA under conditions suitable to form a second complex of neutrophil and ANCA; and assaying for the presence or absence of a pANCA staining pattern by detecting the presence or absence of the second complex, where the presence of the first complex and the presence of a pANCA staining pattern indicate the presence of pANCA, provided that detection of the first complex is not by histological means.

In another embodiment, the invention provides a method of diagnosing clinical subtypes of CD by determining the presence of pANCA and SAPPA by obtaining a serum sample from the patient with CD; contacting the serum sample diluted at least about 100-fold with antigen specific for ANCA under conditions suitable to form a first complex of antigen and ANCA; detecting the presence or absence of the first complex; contacting an appropriate dilution of the serum sample with antigen specific for ANCA under conditions suitable to form a second complex of antigen and ANCA; and assaying for the presence or absence of a pANCA staining pattern and for the presence or absence of a SAPPA staining pattern by detecting the presence or absence of the second complex, where the presence of the first complex and the presence of a pANCA staining pattern indicate the presence of pANCA and where low level ANCA-positivity indicated by a low level of the first complex and the presence of a SAPPA staining pattern indicate the presence of SAPPA, provided that detection of the first complex is not by histological means.

Another embodiment of the invention involves determining whether pANCA is DNase-sensitive by DNase treatment of neutrophils in assays such as ELISA and immunofluorescence to elicit the loss of a positive control value. The control is the result of repeating the process on a sample from the same source, except that the neutrophils are not subjected to DNase treatment.

As used herein, the term "DNase-sensitive," when used in reference to pANCA, means that the presence of pANCA is lost or substantially diminished upon treatment with DNase under conditions resulting in substantially complete digestion of cellular DNA with significant loss of nuclear or cellular morphology. Substantially complete digestion of cellular DNA means that digestion of cellular DNA such that the cellular DNA has substantially lost its ability to bind proteins and other cellular materials normally associated with the cellular DNA of the neutrophil. One skilled in the art understands that neutrophils, for example, are rendered permeable to DNase by permeabilization such as alcohol-fixation prior to treatment with DNase.

Conditions sufficient to cause substantially complete digestion of cellular DNA will vary in accordance with the purity and concentration of the DNase used and include, for example, incubating the immobilized neutrophil in a concentration of DNase of about 2 to 10 units of DNase per milliliter of a suitable buffer for a time in the range of about 15 minutes to one hour at a temperature in the range of about 22° C. to 40° C. A variety of preparations of purified Dnase are available, for example, from Boehringer Mannheim (Indianapolis, Ind.) or from Promega Corporation (Madison, Wis.).

The invention further provides a method of diagnosing clinical subtypes of Crohn's disease in a patient with CD by determining the presence or absence of ANCA, pANCA and SAPPA in the patient with CD and determining the presence or absence of ASCA in the patient with CD, where the presence of pANCA combined with the absence of ASCA indicate a clinical subtype of CD with features of UC, the presence of SAPPA indicates a clinical subtype of CD having perforating, fistulizing or small bowel obstructive disease, and the presence of ASCA combined with the absence of ANCA indicates a clinical subtype of CD lacking features of ulcerative colitis and having perforating, fistulizing or small bowel obstructive disease.

As disclosed herein, serum ANCA and serum ASCA can be used together to diagnose clinical subtypes of Crohn's disease. As described in Example II, sera from patients with an established diagnosis of Crohn's disease were analyzed with respect to serum ANCA and ASCA levels and for the presence of particular ANCA staining patterns. ANCA levels were determined using a fixed neutrophil ELISA assay, and staining patterns were established using indirect immunofluoresence as set forth in Example III. The clinical profiles summarized in Table 5 demonstrate that the presence of pANCA indicates a clinical subtype of CD with features of ulcerative colitis. A distinct clinical subtype was indicated by the presence of SAPPA. As shown in Table 5, the SAPPA subtype of CD is characterized by aggressive disease, and particularly by a high frequency of perforating or fistulizing disease (68%) or small bowel obstructive disease (59%). A third clinical subtype was indicated by the presence of serum ASCA in combination with the absence of serum ANCA. As disclosed herein, the ASCA-positive, ANCA-negative subtype of CD is characterized as infrequently having features of ulcerative colitis (33%) and frequently having perforating or fistulizing disease (63%) or small bowel obstructive disease (75%). In sum, these results show that serum ANCA, alone or in combination with serum ASCA, is diagnostic of particular clinical subtypes of Crohn's disease.

The invention provides, for example, a method of diagnosing clinical subtypes of Crohn's disease by obtaining a serum sample from the patient with CD; contacting the serum sample diluted at least about 100-fold with antigen specific for ANCA under conditions suitable to form a first complex of antigen and ANCA; detecting the presence or absence of the first complex; contacting an appropriate dilution of the serum sample with antigen specific for ANCA under conditions suitable to form a second complex of antigen and ANCA; and assaying for the presence or absence of a pANCA staining pattern and for the presence or absence of a SAPPA staining pattern by detecting the presence or absence of the second complex, where the absence of the first complex indicates the absence of ANCA, the presence of the first complex and the presence of a pANCA staining pattern indicate the presence of pANCA and where low level ANCA-positivity indicated by a low level of the first complex and the presence of a SAPPA staining pattern indicate the presence of SAPPA, provided that detection of the first complex is not by histological means.

Anti-*Saccharomyces cerevisiae* antibodies (ASCA) are characteristically elevated in patients having Crohn's disease although the nature of the *S. cerevisiae* antigen supporting the specific antibody response in CD is unknown (Sendid et al., *Clin. Diag. Lab. Immunol.*, 3:219–226 (1996), which is incorporated herein by reference). These antibodies may represent a response against yeasts present in common food or drink or a response against yeasts that colonize the gastrointestinal tract. Studies with periodate oxidation have shown that the epitopes recognized by ASCA in CD patient sera contain polysaccharides. Oligomannosidic epitopes are shared by a variety of organisms including different yeast strains and genera, filamentous fungi, viruses, bacteria and human glycoproteins. Thus, the mannose-induced antibody responses in CD may represent a response against a pathogenic yeast organism or may represent a response against a cross-reactive oligomannosidic epitope present, for example, on a human glycoprotein autoantigen. Regardless of the nature of the antigen, elevated levels of serum ASCA are a differential marker for Crohn's disease, with only low levels of ASCA reported in UC patients (Sendid et al., supra, 1996).

Anti-*Saccharomyces cerevisiae* antibodies (ASCA), as disclosed herein, are a serum marker characteristically elevated in patients with particular clinical subtypes of Crohn's disease. The results set forth in Example II that the presence of serum ASCA combined with the absence of serum ANCA is diagnostic of a clinical subtype of Crohn's disease infrequently having features of ulcerative colitis but often having perforating, fistulizing disease or small bowel obstructive disease (see Table 5). Thus, serum ASCA, in combination with serum ANCA can be used to diagnose distinct clinical subtypes of Crohn's disease, which may share similar types of inflammation and responses to therapies.

As used herein, the term "antigen specific for ASCA" refers to any antigen or mixture of antigens that is bound specifically by ASCA. Although ASCA antibodies were initially characterized by their ability to bind *S. cerevisiae*, those of skill in the art will understand that an "antigen specific for ASCA" can be obtained from *S. cerevisiae*, or can be obtained from a variety of other sources so long as the antigen is capable of binding specifically to ASCA antibodies. Accordingly, exemplary sources of an antigen specific for ASCA contemplated for use in the methods of the invention include whole killed yeast cells, such as from the genera Saccharomyces and Candida, yeast cell wall phosphopeptidomannan (PPM), oligomannosides, neoglycolipids, anti-ASCA idiotypic antibodies, and the like. As described above, different species and strains of yeast, including Saccharomyces, can be used as an antigen specific for ASCA in the methods provided herein. For example, *S. cerevisiae* strain Su1, Su2, CBS 1315 or BM 156, or *Candida albicans* strain VW32, can be used as an antigen specific for ASCA in the methods of the invention.

Preparations of yeast cell wall mannans, or phosphopeptidomannans (PPM), are also contemplated herein as antigens specific for ASCA. These water soluble surface antigens can be prepared by appropriate extraction techniques, including autoclaving as described in Example IV or can be obtained commercially (see Lindberg et al., *Gut* 33:909–913 (1992), which is incorporated herein by reference). The acid stable fraction of yeast cell wall PPM also can be useful in the methods of the invention (Sendid et al., supra, 1996). An exemplary PPM for use in diagnosing clinical subtypes of Crohn's disease is derived from *S. uvarum* strain ATCC #38926.

Purified oligosaccharide antigens, such as oligomannosides specific for ASCA, also are contemplated for use in the methods of the invention. For use herein, the purified oligomannoside antigens are preferably converted into neoglycolipids as described in Faille et al., *Eur. J. Microbiol. Infect. Dis.* 11:438–446 (1992). One skilled in the art understands that the reactivity of such an oligomannoside antigen with ASCA can be optimized by varying the mannosyl chain length (Frosh et al., *Proc. Natl. Cad. Sci. USA*, 82:1194–1198 (1985)); the anomeric configuration (Fukazawa et al., In E. Kurstak (ed.), *Immunology of Fungal Disease*, Marcel Dekker Inc., New York, pp. 37–62 (1989); Nishikawa et al, *Microbiol. Immunol.*, 34:825–840 (1990);

Poulain et al., *Eur. J. Clin. Microbiol*, 23:46–52 (1993); Shibata et al., *Arch. Biochem. Biophys.*, 243:338–348 (1985); and Trinel et al., *Infect. Immun.*, 60:3845–3851 (1992)); or the position of the linkage (Kikuchi et al., *Planta*, 190:525–535 (1993)). Each of the foregoing references are incorporated herein by reference in their entirety.

In a particular embodiment of the present invention, an oligomannoside antigen specific for ASCA includes the mannotetraose Man(1→3)Man(1→2)Man(1→2)Man, and can be purified from PMM as described in Faille et al., supra, 1992. An exemplary neoglycolipid for use in the invention methods can be constructed by releasing the oligomannoside from its respective PPM and subsequently coupling the released oligomannoside to 4-hexadecylaniline or the like, as set forth in Example V.

As used herein, the term "secondary antibody selective for ASCA" means an antibody or combination of antibodies, which binds ASC. Preferably, a secondary antibody does not compete with antigen for binding to ASCA. A secondary antibody can be, however, an anti-ASCA antibody that binds any epitope of ASCA. A particularly useful secondary antibody is an anti-IgA antibody or anti-Ig antibody, or combination thereof, having specificity for the class determining portion of ASCA. Preferably, a secondary antibody selective for ASCA is a combination of anti-IgA antibody and anti-IgG antibody. As set forth herein, an ASCA-positive patient is a patient having either IgA or IgG serum ASCA or both.

Further provided by the present invention are kits for diagnosing clinical subtypes of CD, which contain neutrophil and antigen specific for ASCA. The neutrophil can be, for example, alcohol-fixed neutrophil such as ethanol-fixed neutrophil or methanol-fixed neutrophil. The antigen specific for ASCA can be, for example yeast cell wall PPM, such as yeast cell wall PPM extracted by autoclaving. The yeast cell wall can be prepared from *S. uvarum*, for example, strain ATCC #38926. If desired, one or more secondary antibodies selective for ASCA, such as anti-IgA or anti-IgG, or a combination thereof, can be included in a kit of the invention. Similarly, if desired, one or more secondary antibodies selective for ANCA, such as anti-IgG, also can be included in a kit of the invention.

The following examples are intended to illustrate but not limit the present invention.

EXAMPLE I

Comparison of the Clinical Feature of pANCA-Positive and pANCA-Negative CD Patients This example demonstrates that the pANCA status of Crohn's disease patients correlates with a clinical subtype of Crohn's disease having features of ulcerative colitis.

A. Determination of Patient ANCA Status by ELISA and Indirect Immunofluorescence Assay Presence of ANCA was determined by Fixed Neutrophil ELISA A fixed neutrophil enzyme-linked immunosorbent assay was used to detect ANCA as described in Saxon et al., supra, 1990, which is incorporated herein by reference, and all samples were analyzed in a blinded fashion. Microliter plates were coated with $2.5 \times 10^5$ neutrophils per well and treated with 100% methanol to fix the cells. Cells were incubated with 0.25% bovine serum albumin (BSA) in phosphate-buffered saline to block nonspecific antibody binding. Next, control and coded sera were added at a 1:100 dilution to the bovine serum/phosphate-buffered saline blocking buffer. Alkaline phosphatase conjugated goat F(ab')$_2$ anti-human immunoglobulin G (γ-chain specific) antibody (Jackson Immunoresearch Labs, Inc., West Grove, Pa.) was added at a 1:1000 dilution to label neutrophil bound antibody. A p-nitrophenol phosphate substrate solution was added and color development was allowed to proceed until absorbance at 405 nm in the positive control wells was 0.8–1.0 optical density units greater than the absorbance in blank wells. The results were expressed as percent of standard binding with pANCA-positive defined as greater than two standard deviations (SD) above mean of control. Titers were also determined.

Indirect Immunofluorescence Assay for Determination of ANCA Staining Pattern

Indirect immunofluorescent staining was performed on samples that were ANCA-positive by ELISA to determine whether the predominant staining pattern was perinuclear (pANCA) or cytoplasmic (cANCA). Glass slides containing approximately 100,000 neutrophils per slide were prepared by cytocentrifugation (Shandon Cytospin, Cheshire, England) and they were fixed in 100% methanol, air-dried, and stored at −20° C. The fixed neutrophils were incubated with human sera were diluted (1:20), and the reaction was visualized with fluorescein-labeled F(ab')$_2$ γ chain-specific antibody as described in Saxon et al., supra, 1990. The slides were examined using an epifluorescence-equipped Olympus BH-2 microscope (Olympus, Lake Success, N.Y.).

Characteristics of Anti-Neutrophil Cytoplasmic Antibodies from CD Patients

Serum ANCA was detected in 38/69 (55%) of the CD study population. ANCA-positive CD patients demonstrated a slight predominance of cytoplasmic staining (53%) as compared to periplasmic staining (47%), although this did not reach statistical significance ($p_c$=0.75). The mean ELISA binding level of the pANCA-positive CD serum samples (41±6) was higher than those that were cANCA-positive (16±1; p<0.000001) or ANCA-negative (6±1; p<0.000001) (see FIG. 1). Provided at the right of FIG. 1 for comparison are mean binding levels of historical ANCA-positive controls as described by Duerr et al., *Gastroenterol*. 100:1590–1596 (1991), which is incorporated herein by reference. The pANCA-positive and cANCA-positive subgroups are denoted "p" and "c," Comparison of the mean ELISA binding levels of the pANCA-positive, cANCA-positive, and ANCA-negative CD subgroups to historical means for ANCA+ UC patients from data by Duerr et al., supra, 1991 (pANCA-positive UC:65±6; cANCA+ UC:36±2), indicated that ANCA is present at lower levels in ANCA+ CD patients than ANCA+UC patients. The mean titer of the pANCA-positive CD subgroup (512±87) was higher than that of the cANCA+ subgroup (227±25) (p=0.0024).

Statistical Analysis

Statistical analysis was performed using Student's t tests for comparisons of quantitative variables between two groups. Yate's continuity corrected $\chi^2$ tests, denoted by $p_c$, were used for comparisons of qualitative variables between two or more groups. When the expected number of a cell is less than 5, Fisher's exact tests were also calculated for comparisons between two proportions and corresponding p-values were denoted by $p_{Fisher's\ exact}$. Log transformations were performed for ANCA titers to obtain a normal distribution for hypothesis testing.

B. Clinical Symptoms of pANCA-Positive and pANCA-Negative CD Patients

Clinical Assessment and Characterization of Crohn's Disease Patients

Clinical information for 69 CD patients was collected by chart review and patient interview by clinical investigators who were blind to individual patient ANCA status. Epidemiological data included: age, age at onset of IBD symptoms, disease duration, gender, ethnicity, and family history of IBD. For each patient, all areas of endoscopically, surgically, histopathologically, or radiographically documented inflammation, stricturing, fistulization, or perforation were recorded. For purpose of analysis, anatomic location of disease was further grouped into categories of "small bowel disease only," "ileocolonic disease," and "colonic involvement only." Signs and symptoms associated with active Crohn's disease were noted, including: obstructive symptoms, diarrhea, bleeding and mucus discharge, urgency, tenesmus, perianal abscess or fistula, anal fissures or strictures, as well as extraintestinal manifestations of IBD. Pharmacological interventions were grouped to reflect the use of sulfasalazine or oral 5-ASA products; immunomodulatory agents such as 6-mercaptopurine/azathioprine, methotrexate, cyclosporin or anti-TNF antibody therapy; IBD-directed antibiotic therapy; or topical therapy for distal colonic disease such as enemas, foams or suppositories. Steroid use was noted and further quantified into estimated total years of systemic corticosteroid exposure, termed "steroid years." The number, type, and reason for all IBD-related surgeries also was recorded.

CD patients were examined for "features of ulcerative colitis." Features of ulcerative colitis were defined as clinical features of left-sided colonic disease, including a combination of the typical left-sided features outlined in Table 2, section A, which are further corroborated by the endoscopic or histopathologic features listed in Table 2, sections B and C. Patients exhibiting these features characteristic of left-sided or distal UC, have features of UC.

Pathology reports were obtained in 93% of the total study population (100%, 85% and 94% of pANCA-positive, cANCA-positive, and ANCA-negative CD subgroups, respectively). Actual biopsies or surgical specimens were available for review by one of two pathologists with IBD expertise in 42% of the overall CD population (61%, 30%, and 35% of pANCA-positive, cANCA-negative, and ANCA-negative CD subgroups, respectively). Special attention was paid to the character of inflammatory process (homogeneous/continuous versus focal inflammation within and between biopsy specimens), the depth of inflammation (superficial versus extension into submucosa or transmural inflammatory process), and the presence or absence of granulomas and crypt abscesses.

Distribution of Clinical and Epidemiological Characteristics of Crohn's Disease Stratified According to ANCA Status A comparison of the clinical and epidemiological characteristics of the pANCA-positive CD, cANCA-positive CD, and ANCA-negative CD subgroups is depicted in Table 3. No significant relationship was detected between the presence of pANCA or cANCA and age, age of onset, disease duration, gender, or family history of IBD ($p_c>0.05$). More patients were of Jewish descent in the cANCA-positive subgroup than in the ANCA-negative group ($p_c=0.025$). There was no significant difference in frequency of perforating or fistulizing disease in the pANCA-positive subgroup ($p_c>0.10$). There was no significant difference in disease severity between the subgroups, as reflected by numbers of surgeries or years of exposure to systemic steroid therapy ($p_c>0.05$). The majority of CD patients in all three oups required immunomodulation.

Figure 2:
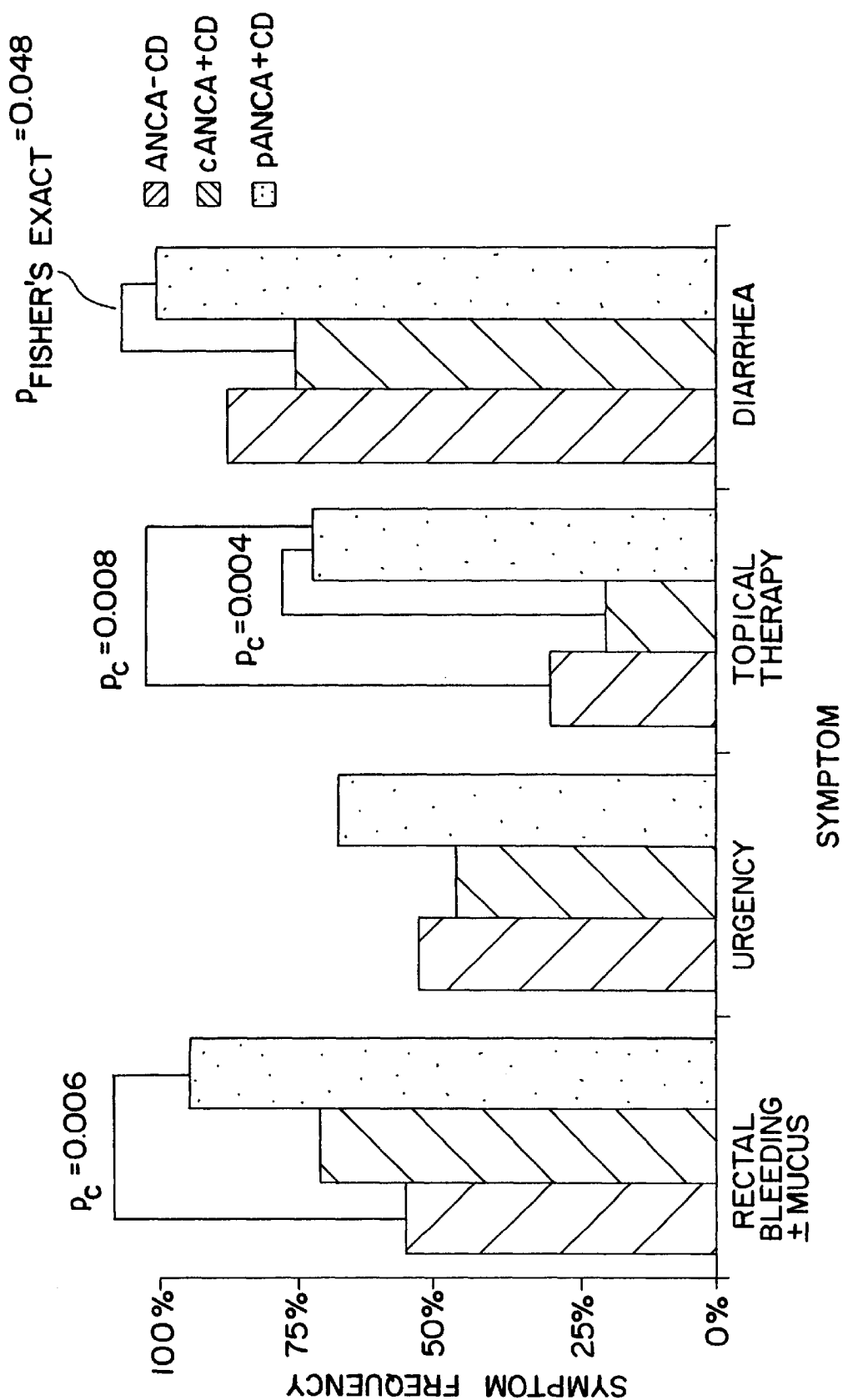
FIG. 2 shows the clinical symptoms of a Crohn's disease study population of 69 patients. The differences between groups without p-values are not statistically significant.

Frequency of Clinical Symptoms of left-sided Colonic Inflammation in pANCA-positive Crohn's Disease Patients Crohn's disease patients who were pANCA positive more often exhibited rectal bleeding and mucus discharge, than did t ANCA-negative CD subgroup ($p_c=0.006$) or the cANCA-positive CD sub oup ($p_{Fisher's\ exact}=0.09$) as shown in FIG. 2. A trend towards in creased urgency was also evident in the pANCA-positive subgroup. The higher prevalence of left-sided symptoms in the pANCA-positive subgroup as compared with the ANCA-negative and cANCA-positive subgroups was refleccted in the higher percent of pANCA-positive patients having been treated with topical agents ($p_c=0.008$ and $p_c=0.004$, respectively). A greater number of pANCA-positive CD patients experienced diarrhea than those in the cANC-positive CD ($p_{Fisher's\ exact}=0.048$) and the ANCA-negative CD $p_c>0.112$) subgroups. Thus, symptoms of left-sided colonic inflammation such as rectal bleeding and mucous discharge, urgency, and treatment with local topica5-ASA or steroid therapies were more often present in pANCA-positive CD patients. Characteristic features of Crohn's disease exhibited by the pANCA+ CD patients are highlighted in Table 4.

pANCA-positive Crohn's Disease Patients do not have Isolated Small Bowel Inflammation The anatomic location of documented Crohn's disease involvement for the pANCA-positive, cANCA-positive, and ANCA-negative CD subgroups was categorized into "small bowel disease on y", "ileocolonic disease", and "colonic involvement only." Ileocolonic involvement was observed in fifty percent of pANCA-positive CD patients, a the disease was limited to the colon in the other fifty percent. No patient in the pANCA-positive CD subgroup had disease limited to the small bowel. Similarly, small bowel obstructive symptoms were exhibited less frequently in the pANCA-positive subgroup than in the other subgroup PS, although this difference did not reach statistical significance.

Figure 3:
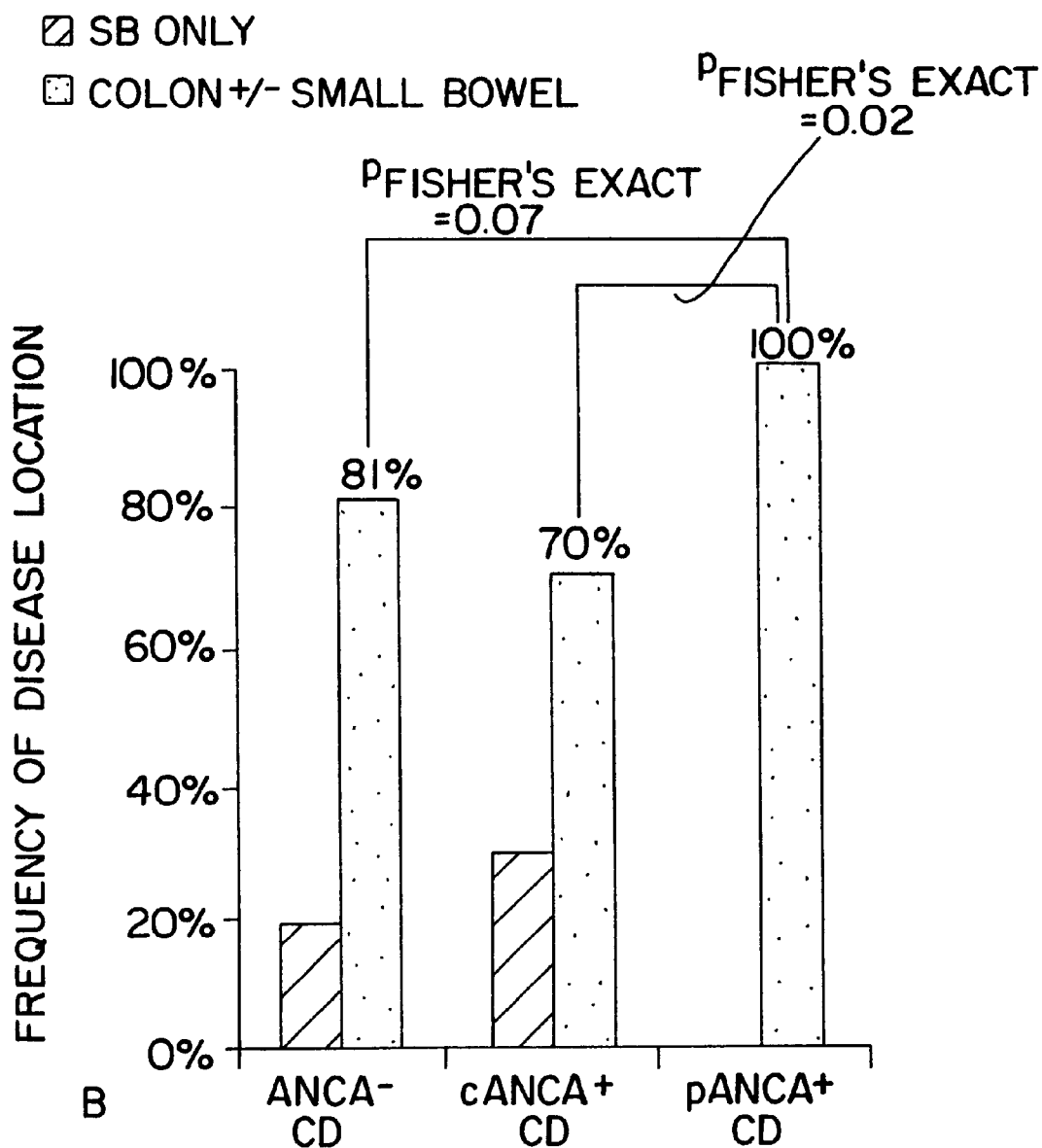
FIG. 3 shows the anatomic distribution of disease by ANCA-negative, cANCA-positive and pANCA-positive CD subgroups. Colonic involvement, with or without small bowel disease, was present in the majority of CD patients within each subgroup.

Expression of Serum pANCA is not Related Solely to the Presence of Colonic Disease Colonic inflammation such as ileocoloni disease or colonic involvement only was present in 83% of the CD study population as shown in FIG. 3. The majority of patients in each subgroup had colonic involvement: 100% of the pANCA-positive CD subgroup, 70% oft e cANCA-positive CD subgroup, and 81% in the ANCA-negative CD subgroup). There was no statistically significant difference between the proportion of pANCA-positive and ANCA-negative patients with colonic disease ($p_{Fisher's\ exact}=0.07$). Of all CD patients with colonic involvement, 32% were pANCA-positive, while the majority of CD patients with colitis (68%) did not e press serum pANCA. Thus, the expression of serum pANCA, is not relate solely to the presence of colonic disease.

Left-sided Colitis is present in all pANCA-Positive Crohn's Disease Patients

Endoscopic or histopathologic inflammation of the rectum or sigmoid colon was present in every pANCA-positive CD patient. The frequency of endoscopically or histopathologically documented left-sided colitis was significantly different when compared either the ANCA-negative ($p_c=0.002$) or cANCA+($p_{Fisher's\ exact}=0.001$) subgroup. There was no difference between the latter two subgroups ($p_c=1$).

TABLE 3

| Patient | Confirmed Small Bowel Disease* | Perianal Fistula Abscess | Other Fistula/ Abscesses | Anal Disease | Endoscopic & Histopathologic | Submucosal or Transmural Inflammation | Granulomas | Other |
|---|---|---|---|---|---|---|---|---|
| 1 | String sign in distal TI | | | | | | | oral AU's |
| 2 | | F | | Indurated, Inflamed | Cobblestoning; Endoscopic skip lesions | Y | Y | |
| 3 | Cobblestoning of distal TI; Anastomotic stenosis | | TI perforation; 10 yrs later - Anastomatic A | | Anastomotic ulcerations & S; Asymmetric inflammation; Deep fissures; Linear ulcers | Y | Y | s |
| 4 | | Multiple F's & A's | Recto-vaginal | Induration; S; Fissure; Tags | Linear/seripiginous ulcerations; Tight S in sigmoid | | Y | |
| 5 | | | | | Endoscopic & histologic skip lesions | Y | | |
| 6 | | | | | Endoscopic skip lesions | Y | Y | |
| 7 | Multiple high-grade ileal S's following two resections for SBO | | | | Endoscopic skip lesions | Y | | |
| 8 | | | | | Deep, discrete ulcers within normal mucosa; Discontinuous, asymmetric inflammation | Y | Y | |
| 9 | | F | | Fissure | Histologic skip regions; Cobblestoning; Deep & linear ulcers; Asymmetric inflammation | Y | Y | |
| 10 | | | | | Histologic skip lesions | Y | Y | |
| 11 | | | | | Endoscopic & histologic skip lesions | | Y | |
| 12 | Ulcerations in TI; Recurrent anastomotic ulceration | Multiple F's | Enterocutaneous A/F | Tags | Discontinuous, asymmetric inflammation; Cobblestoning | Y | Y | oral AU's |
| 13 | | F | Peripouch F/A | Anal ulcers; Fissure | Recurrence in pouch; Cobblestoning; Stricture at pouch-anal anastososis | | | |
| 14 | | | | | Deep, discrete ulcers within normal mucosa, Discontinuous, asymmetric inflammation | Y | | |
| 15 | Inflamed, stenotic TI | | "Microperforation" | | Undermining, serpiginous ulcers, Discontinuous, asymmetric inflammation, Cobblestoning | | | oral AU's |
| 16 | TI ulcerations, nodularity and stenosis; Jejunal filing defects | | | | | | | oral AU's |
| 17 | Linear ulcerations and stenosis in distal ileum | | | | | | | |
| | TI ulceration & S | | | | Discrete ulcers within normal mucosa, Haloscopic | | | |
| 18 | | | | | skip lesions, Deep linear ulcerations | | | oral AU's |
| | | | | | Discrete ulcers within normal mucosa, Histologic skip lesions; deep linear ulcerations | | | |
| | 8/18 (44%) | 5/18 (26%) | 5/18 (28%) | 4/18 (22%) | 16/18 (89%) | 10/16 (56%) | 9/18 (50%) | 5/18 (28%) |

TI = Terminal ileum; S = Stricture; SB = Small bowel; SBO = Small bowel obstruction; F = Fistula; A = Abscess; AU = Aphthous ulcers
Small bowel diseaae confirmed by radiographic, endoscopic, and/or surgical evaluations pANCA-Positive CD Patients have Features of Ulcerative Colitis The absence of Crohn's involvement limited to the small bowel and the clinical expression of symptoms of left-sided colonic inflammation, along with documented left-sided colitis are all features consistent with ulcerative colitis. In addition to their other features of CD, a subset of the CD study population was noted to have features of ulcerative colitis. For these patients with Crohn's disease to be considered to have features of ulcerative colitis, they needed to, at minimum, have rectal bleeding, urgency and tenesmus, which are clinical features of left-sided colonic disease, in combination with a characteristic endoscopic feature (inflammation that is more severe distally than proximally or continuous inflammation or a characteristic histopathologic feature (homogeneous, continuous, predominantly superficial inflammation or lack of "focality" within biopsy specimens). Forty-six percent of all CD patients exhibiting features of ulcerative colitis expressed serum pANCA. In contrast, none of the 30 CD patients lacking these features were pANCA-positive. This difference was highly significant. One hundred percent of pANCA-positive CD patients exhibited features of ulcerative colitis. The number of patients having features of ulcerative colitis as 18/18 (100%) in the pANCA-positive CD subgroup; 9/20 (45%) in the cANCA-positive CD subgroup and 12/31 (39%) of patients in the ANCA-negative CD subgroup (see Table 4). Thus, the percent of pANCA-positive CD patients with features of ulcerative colitis was significantly higher than the percent of patients meeting the criteria in either the cANCA-positive or ANCA-negative subgroups.

TABLE 4

Frequency of Features of Ulcerative Colitis in Crohn's Disease Patients Subtyped According to ANCA Status

| Subtype of CD | ANCA-negative CD | cANCA-positive CD | pANCA-positive CD |
|---|---|---|---|
| Frequency of features of UC | 39% | 45% | 100% |

EXAMPLE II

Stratification of Crohn's Disease According to ANCA and ASCA Status

This example demonstrates that Crohn's disease can be subtyped according to ANCA and ASCA status.

This study involved 89 patients with an stablished diagnosis of CD as determined by a combination of characteristic clinical, radiographic, endoscopic & histopathologic criteria. Sera collected from these patients were examined in a blinded fashion for the presence of ANCA and ASCA. ANCA was determined using the fixed neutrophil ELISA asssy, and levels were determined and expressed as ELISA units (Eu). Using indirect immunofluorescence (IIF) staining, ELISA-positive samples were further stratified into one of three patterns: 1) DNase-positive pANCA, which is a pattern sensitive to DNase (DNase-positive pANCA); 2) cytoplasmic ANCA (cANCA) and 3) SAPPA, a pattern characterized by diffuse staining with speckling across the neutrophil. Serum samples exhibiting either IgG or IgA ASCA reactivity were termed ASCA-positive. Clinical profiles were generated by investigators blinded to serum marker status.

TABLE 5

Stratification of Crohn's Disease According to ANCA and ASCA Status

|  | DNase+ pANCA ASCA− n = 19 | DNase+ pANCA n = 26 | cANCA n = 17 | SAPPA n = 22 | ANCA− n = 24 |
|---|---|---|---|---|---|
| ELISA ANCA± | 100% | 100% | 100% | 100% | 0 |
| ANCA (Mean ± SD) | 66 ± 33 | 67 ± 33 | 37 ± 11 | 24 ± 14 | 9 ± 4 |
| ASCA+ | 0 | 7 (27%) | 5 (29%) | 12 (55%) | 17 (71%) |
| "UC-like" | 19 (100%) | 24 (92%) | 11 (65%) | 14 (64%) | 8 (33%) |
| Perf/Fist Dis | 7 (37%) | 11 (42%) | 8 (47%) | 15 (68%) | 15 (63%) |
| Small Bowel Obstructive Symptoms | 5 (26%) | 9 (35%) | 11 (65%) | 13 (59%) | 18 (75%) |
| Immunosup Therapy | 19 (68%) | 19 (73%) | 11 (65%) | 18 (82%) | 19 (79%) |

Each of the subgroups were similar with respect to age, age of onset, and disease duration. As shown in Table 5, the mean ANCA level was highest in the DNase-positive pANCA subgroup and lowest in the ANCA-negative group. There was a negative correlation between mean ANCA levels and levels of ASCA expression. The incidence of small bowel obstructive disease was highest in the ANCA-negative group and lowest in the DNase-positive pANCA subgroup that did not express ASCA. Of those patients who were DNas-positive pANCA and ASCA-negative, one hundred percent had clinical features of ulcerative colitis.

These results provide further evidence of heterogeneity within CD. Patients with CD can now be stratified based on ANCA subtypes as well as ASCA status. Assaying for these markers in a population with less severe disease that does not require immunosuppressive therapy, can extend these subgroups.

EXAMPLE III

Determination of Patient ANCA Status

This example demonstrates the determination of patient ANCA status by ELISA and indirect immunofluoresence. Fixed neutrophil ELISA for Determining ANCA Levels A fixed neutrophil enzyme-linked immunosorbent assay was used to detect ANCA as described in Saxon et al., supra, 1990, which is incorporated herein by reference, and all samples were analyzed in a blinded fashion. Briefly, microtiter plates were coated with $2.5 \times 10^5$ neutrophils per well and treated with 100% methanol to fix the cells. Cells were incubated with 0.25% bovine serum albumin (BSA) in phosphate-buffered saline to block nonspecific antibody binding. Next, control and coded sera were added at a 1:100 dilution to the bovine serum/phosphate-buffered saline blocking buffer. Alkaline phosphatase-conjugated goat F(ab')$_2$ anti-human immunoglobulin G antibody (γ-chain specific; Jackson Immunoresearch Labs, Inc., West Grove, Pa.) was added at a 1:1000 dilution to label neutrophil-bound antibody. A solution of p-nitrophenol phosphate substrate was added, and color development was allowed to proceed until absorbance at 405 nm in the positive control wells was 0.8–1.0 optical density units greater than the absorbance in blank wells.

Sera from 20 normal individuals was used to define negative binding. The mean reading of the normal control sera was about 5 to 15 ELISA units; the mean plus two standard deviations ranged from 10 to 25 ELISA units. Standard binding of pooled, well-characterized pANCA-positive UC patient sera was set to 100 ELISA units, and results with test patient sera were expressed relative to this standard positive binding. Samples were defined to be ANCA-positive when ELISA levels were greater than two standard deviations (SD) above the mean of the pooled normal control sera. Low level ANCA-positivity was defined as less than about 40 ELISA units.

Indirect Immunofluorescence Assay for Determination of ANCA Staining Pattern

Indirect immunofluorescent staining was performed on samples that were ANCA-positive by ELISA to determine whether the predominant staining pattern was perinuclear (pANCA); cytoplasmic (cANCA); or diffuse with speckling (SAPPA). Glass slides containing approximately 100,000 neutrophils per slide were prepared by cytocentrifugation (Shandon Cytospin, Cheshire, England). The slides were subsequently fixed in 100% methanol, air-dried and stored at −20° C. The fixed neutrophils were incubated with human sera diluted 1:20 in PBS with 0.25% bovine serum albumin and 0.2% sodium azide. The reaction was visualized with a 1:1000 dilution of fluorescein-labeled F(ab')$_2$ γ chain-specific antibody as described in Saxon et al., supra, 1990. Slides were examined using an epifluorescence-equipped Olympus BH-2 microscope (Olympus, Lake Success, N.Y.).

Figure 4A:
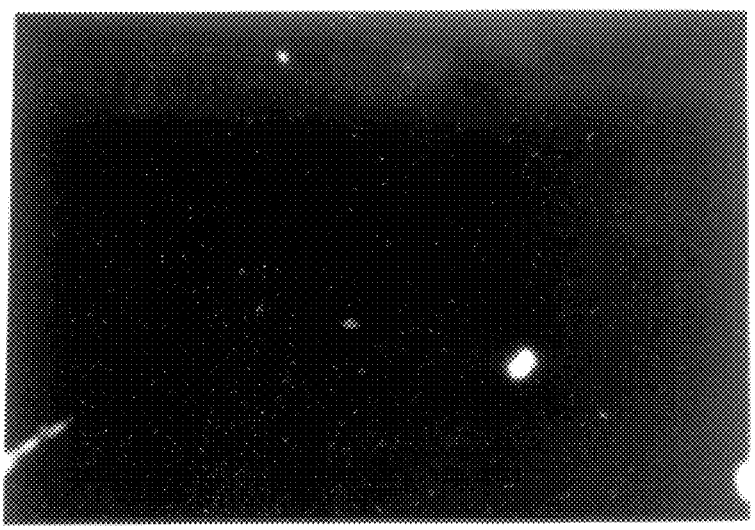
FIG. 4 shows immunofluorescence of methanol-fixed neutrophil with human sera. Panel (a) shows an ANCA-negative staining pattern; panel (b) shows the pANCA staining pattern; and panel (c) shows the SAPPA staining pattern.
Figure 4B:
Figure 4C:
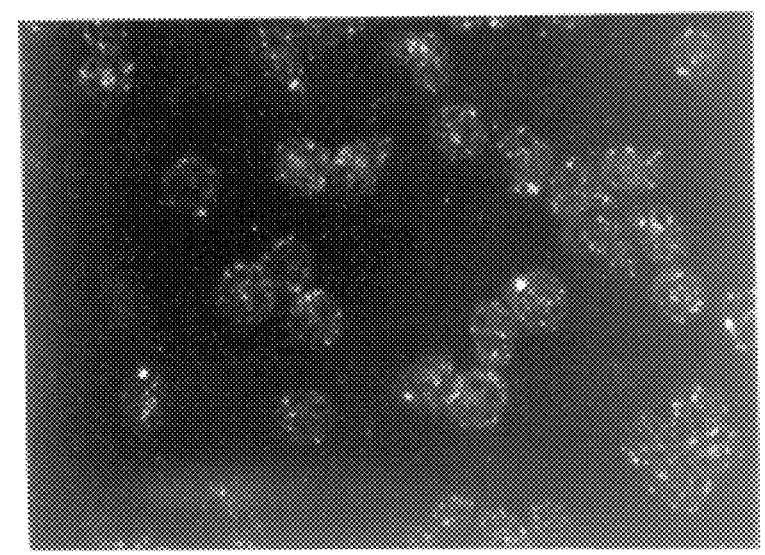

Upon indirect immunofluorescence, ANCA-positive samples gave several distinct staining patterns as shown in FIG. 4. In contrast to the absence of staining seen with sera that was ANCA-negative, i.e. less than two standard deviations above the mean of normal sera as shown in panel (a), ANCA-positive samples produced distinct patterns of reactivity with human neutrophil. Nuclear/perinuclear staining of ANCA-positive samples is shown in panel (b) and is designated pANCA. A distinct, diffuse staining pattern with speckling over the entire neutrophil was produced by some low-level ELISA-positive samples (SAPPA). Panel (c) shows representative staining for this SAPPA pattern. A distinct cytoplasmic staining pattern was evident with other ANCA-positive sera (cANCA; data not shown).

EXAMPLE IV

ASCA Elisa Assay

This example demonstrates that the presence of anti-Saccharomyces cerevisiae antibodies in patient sera can be determined using an ELISA microplate assay.

Preparation of Yeast Cell Wall Mannan

Yeast cell wall mannan was prepared as follows and as described in Faille et al. Eur. *J. Clin. Microbiol. Infect. Dis.* 11:438–446(1992) and in Kocourek and Ballou et al., *J. Bacteriol* 100:1175–1181(1969), each of which is incorporated herein by reference. A lyophilized pellet of yeast Saccharomyces uvarum was obtained from the American Type Culture Collection (#38926). Yeast were reconstituted in 10 ml 2X YT medium, prepared according to Sambrook et al., *Molecular Cloning* Cold Spring Harbor Laboratory Press (1989), which is incorporated herein by reference. S. uvarum were grown for two to three days at 30° C. The terminal S. uvarum culture was inoculated on a 2X YT agar plate and subsequently grown for two to three days at 30° C. A single colony was used to inoculate 500 ml 2X YT media, and grown for two to three days at 30° C. Fermentation media (pH 4.5) was prepared by adding 20 gm glucose, 2 gm bacto-yeast extract, 0.25 gm $MgSO_4$ and 2.0 ml 28% $H_3PO_4$ per liter distilled water. The 500 ml culture was used to inoculate 50 liters of fermentation media, and the culture fermented for three to four days at 37° C.

S. uvarum mannan extract was prepared by adding 50 ml 0.02 M citrate buffer (5.88 gm/l sodium citrate; pH 7.0+/−0.1) to reach 100 grams of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolve in 6–8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded; then the wash procedure was repeated until the supernatant was colorless, approximately two to three times. The precipitate was collected on a scintered glass funnel, washed with methanol and air dried overnight. On some occasions, the precipitate was collected by centrifugation at 5000 rpm for 10 minutes before washing with methanol and air drying overnight. The dried mannan powder was dissolve in distilled waster, using approximately 5 ml water per gram of dry mannan powder. The final concentration of S. uvarum cell wall mannan was approximately 30 μg/gml.

Preparation of S. uvarum Mannan ELISA Plates

S. uvarum cell mannan ELISA plates were saturated with antigen as follows. Purified S. uvarum mannan prepared as described above was diluted to a concentration of 100 μg/ml with phosphate buffered saline/2% sodium azide (PBS-N3). Using a multi-channel pipettor, 100 μl of 100 μg/ml S. uvarum mannan was added per well of a Costar 96-well hi-binding plate (catalogue number 3590; Costar Corp., Cambridge, Mass.). The antigen as allowed to coat the plate at 4° C. for a minimum of 12 hours. Each lot of plates was compared to a previous lot before use. Plates were stored at 2–8° C. for up to one month.

Analysis of Patient Sera

Patient sera were analyzed in duplicate for a anti-IgG or anti-IgA reactivity. Microtiter plates saturated with antigen as described above were incubated with phosphate buffered saline/0.05% Tween-20 for 45 minutes at room temperature to inhibit nonspecific antibody binding. Patient sera were subsequently added at a dilution of 1:800 for IgG and 1:80 for IgA and incubated for 1 hour at room temperature. Wells were washed three times with PBS/0.05% Tween-20. Then a 1:1000 dilution of alkaline phosphatase-conjugated goat anti-human IgG $F(Ab)_2$ (Pierce, Rockford, Ill.) or a 1:1000 dilution of alkaline phosphatase-conjugated goat anti-human IgA (Jackson Immunoresearch, Westgrove, Pa.) was added, and the microtiter plates incubated for 1 hour at room temperature. A solution of p-nitrophenol phosphate in diethanolamine substrate buffer was added, and color development allowed to proceed for 10 minutes. Absorbance at 405 nm was analyzed using an automated EMAX plate reader (Molecular Devices, Sunnyvale, Calif.).

Standard binding of pooled sera from patients with an established diagnosis of Crohn's disease was used as a standard reference for binding and set to be 100 ELISA units. Results with test patient sera were expressed as a percentage of the standard binding of the reference CD sera. ASCA-positivity was defined as anti-IgG ASCA reactivity that was greater than 40% of the reference CD sera or anti-IgA ASCA reactivity that was greater than 20% of the reference CD sera. Using these criteria, samples that were positive with only anti-IgG or only anti-IgA were considered to be ASCA-positive.

EXAMPLE V

Preparation of Purified Antigen Specific for ASCA

This example demonstrates that an oligomannoside can be released from yeast cell wall phosphopeptidomannan and used to produce a neoglycolipid antigen specific for ASCA.

Neoglycolipid antigen specific for ASCA is prepared as follows. Briefly, PPM from an appropriate yeast strain is acetolyze essentially by the method of Hamada et al., supra, (1984). The PPM is dissolved in 10 ml of formamide, mixed with 50 ml of acetic anhydride-pyridine (vol/vol), and heated for 13 hours at 30° C. on a rotary shaker. This solution is then poured into water and centrifuged at 1,500×g for 15 minutes. The pellet is dried, suspended in 50 ml of acetic anhydride-acetic acid (100:100:1), and heated for 13 hours at 40° C. on a rotary shaker. The reaction is stopped by pouring the solution onto ice, and the mixture is neutralized with sodium bicarbonate. The released oligosaccharides are extracted with chloroform, incubated for 15 minutes at room temperature in 10 ml of methanol (adjusted to pH 9 with sodium methoxide), and centrifuged for 15 min at 1,500×g. The pellet is then washed twice in methanol and dissolved in water. The released oligomannosides are separated on a BioGel P2 column (Bio-Rad, Hercules, Calif.; 1.0 by 120 cm). The column is eluted with distilled water at a flow rate of 4 ml/hour at room temperature; approximately 0.6 ml factions are collected and coupled to 4-hexadecylanaline as described in Faille et al., *Infection and Immunity*, 58:3537–3544 (1990), which is incorporated herein by reference.

Neoglycolipids are constructed from oligomannosides released from the cell wall PPM as described above. PPM is depleted in oligosaccharides released after mild acid hydrolysis (oligomannosides linked by phosphodiester bridges) and in oligosaccharides released after β-elimination (oligomannosides linked by O-glycoside bonds to the peptide moiety). This depleted PPM is subsequently acetylated and acetolysed in order to release the polysaccharide side chains according to the method described by Hamada et al., *Applied and Environmental Microbiology*, 48:708–712 (1984); the acetolysis solution is composed of acetic anhydride:acetic acid:sulfuric acid (20:20:1, vol/vol/vol).

The procedure for construction of neoantigens from these oligomannosides is adapted from that described by Tang et al., *Biophysical Research Communications*, 132:474–480 (1985), as previously described (Faille et al., supra, 1990, with slight modifications). Briefly, 100 mg 4-hexadecylaniline (Aldrich Chemical, USA) is added to 500 μl of a solution containing 35 mg sodium cyanoborohydride, 3.5 ml methanol and 400 μl acetic acid. The solution is heated, and 2 mg of oligosaccharides solubilized in 20 μl of water are added. After 90 min at 80° C., the solution is cooled, mixed with 2 ml of chloroform and water (1:1, vol/vol) and centrifuged. The lower phase is discarded. The upper phase is washed again with chloroform (1 ml), dried, dissolved in methanol (2 ml), and centrifuged. The pellet, containing the uncoupled oligosaccharides is discarded.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A method of diagnosing clinical subtypes of Crohn's disease (CD) in a patient with CD, comprising determining whether pANCA or speckling anti-pan polymorphonuclear antibody (SAPPA) is present in said patient with CD, wherein the presence of pANCA indicates a clinical subtype of CD with features of ulcerative colitis and wherein the presence of SAPPA indicates a clinical subtype of CD having perforating, fistulizing or small bowel obstructive disease.

2. The method of claim 1, further comprising determining whether said pANCA is DNase-sensitive, wherein the presence of DNase-sensitive pANCA indicates the clinical subtype of CD with features of ulcerative colitis.

3. The method of claim 1, further comprising:

(a) obtaining a serum sample from said patient with CD;

(b) determining by non-histological means the level of ANCA-positivity in patient sera diluted at least about 100-fold; and (c) assaying for the presence or absence of a pANCA or SAPPA staining pattern, wherein detection of ANCA in patient sera diluted at least about 100-fold and the presence of a pANCA staining pattern indicate the presence of pANCA and wherein detection of low level ANCA positivity in patient sera diluted at least about 100-fold and the presence of a SAPPA staining pattern indicate the presence of SAPPA.

4. The method of claim 1, wherein determining the presence of pANCA and SAPPA comprises:

(a) obtaining a serum sample from the patient with CD;

(b) contacting the serum sample diluted at least about 100-fold with antigen specific for ANCA under condition suitable to form a first complex of antigen and ANCA;

(c) detecting the presence or absence of said first complex;

(d) contacting an appropriate dilution of the serum sample with antigen specific for ANCA under conditions suitable to form a second complex of antigen and ANCA; and (e) assaying for the presence or absence of a pANCA staining pattern and for the presence or absence of a SAPPA staining pattern by detecting the presence or absence of said second complex, wherein the presence of said first complex and the presence of a pANCA staining pattern indicate the presence of pANCA and wherein low level ANCA-positivity indicated by a low level of said first complex and the presence of a SAPPA staining pattern indicate the presence of SAPPA, provided that detection of said first complex is not by histological means.

5. The method of claim 4, wherein said antigen specific for ANCA in step (d) is neutrophil.

6. The method of claim 4, wherein the serum sample in step (b) is diluted 100-fold.

7. The method of claim 4, wherein the presence or absence of said first complex is detected in an immunoassay.

8. The method of claim 7, wherein said immunoassay is an enzyme-linked immunosorbent assay.

9. A method of diagnosing clinical subtypes of Crohn's disease (CD) in a patient with CD, comprising:

(a) determining the presence or absence of ANCA, pANCA and SAPPA in said patient with CD; and (b) determining the presence or absence of anti-*Saccharomyces cerevisiae* antibodies (ASCA) in said patient with CD, wherein the presence of pANCA combined with the absence of ASCA indicate a clinical subtype of CD with features of UC, wherein the presence of SAPPA indicates a clinical subtype of CD having perforating, fistulizing or small bowel obstructive disease, and wherein the presence of ASCA combined with the absence of ANCA indicates a clinical subtype of CD lacking features of ulcerative colitis and having perforating, fistulizing or small bowel obstructive disease.

10. The method of claim 9, further comprising determining whether said pANCA is DNase-sensitive, wherein the presence of DNase-sensitive pANCA combined with the absence of ASCA indicate a clinical subtype of CD with features of UC.

11. The method of claim 9, wherein determining the presence or absence of ANCA, pANCA and SAPPA further comprises:

(a1) obtaining a serum sample from said patient with CD;

(a2) contacting the serum sample diluted at least about 100-fold with antigen specific for ANCA under conditions suitable to form a first complex of antigen and ANCA;

(a3) detecting the presence or absence of said first complex;

(a4) contacting an appropriate dilution of the serum sample with antigen specific for ANCA under conditions suitable to form a second complex of antigen and ANCA; and (a5) assaying for the presence or absence of a pANCA staining pattern and for the presence or absence of a SAPPA staining pattern by detecting the presence or absence of said second complex, wherein the absence of said first complex indicates the absence of ANCA, wherein the presence of said first complex and the presence of a pANCA staining pattern indicate the presence of pANCA and wherein low level ANCA-positivity indicated by a low level of said first complex and the presence of a SAPPA staining pattern indicate the presence of SAPPA, provided that detection of said first complex is not by histological means.

12. The method of claim 11, wherein said antigen specific for ANCA in step (a4) is neutrophil.

13. The method of claim 11, wherein determining the presence or absence of ASCA further comprises:

(b1) contacting said sample with antigen specific for ASCA, under conditions suitable to form a third complex of said antigen specific for ASCA and antibody to said antigen and (b2) detecting the presence or absence of said third complex, wherein the presence of said third complex indcates the presence of ASCA.

14. The method of claim 13, wherein said antigen is yeast cell wall phosphopeptidomannan (PPM).

15. The method of claim 14, wherein said yeast cell wall PPM is *S. uvarum* PPM.

16. The method of claim 15, wherein said yeast cell wall PPM is prepared from strain ATCC #38926.

17. The method of claim 13, wherein the presence or absence of said third complex is detected with one or more secondary antibodies, wherein said one or more secondary antibodies have specificity for a class determining portion of said antibody to said antigen specific for ASCA.

18. The method of claim 17, wherein said one or more secondary antibodies are anti-immunoglobulin A and anti-immunoglobulin G.

19. A kit for diagnosing clinical subtypes of CD, comprising neutrophil and antigen specific for ASCA.

20. The kit of claim 19, wherein said neutrophil is alcohol-fixed neutrophil.

21. The kit of claim 19, wherein said antigen specific for ASCA is yeast cell wall PPM.

22. The kit of claim 21, wherein said yeast cell wall PPM is extracted by autoclaving.

23. The kit of claim 21, wherein said yeast cell wall PPM is *S. uvarum* PPM.

24. The kit of claim 23, wherein said yeast cell wall PPM is prepared from strain ATCC #38926.

25. The kit of claim 19, further comprising one or more secondary antibodies selective for ASCA.

26. The kit of claim 25, wherein said one or more secondary antibodies selective for ASCA are anti-IgG and anti-IgA.

27. The kit of claim 25, further comprising one or more secondary antibodies selective for ANCA.

28. A method of diagnosing a clinical subtype of Crohn's disease in a patient with CD, comprising:

(a) determining the presence or absence of ANCA in said patient with CD; and (b) determining the presence or absence of ASCA in said patient with CD, wherein the presence of ASCA combined with the absence of ANCA indicates a clinical subtype of CD infrequently having features of ulcerative colitis and frequently having perforating, fistulizing or small bowel obstructive disease.

29. The method of claim 28, wherein said ASCA is immunoglobulin A ASCA.

30. The method of claim 28, wherein said ASCA is immunoglobulin G ASCA.

31. The method of claim 28, wherein said ASCA is immunoglobulin A ASCA and immunoglobulin G ASCA.

32. The method of claim 28, wherein the presence or absence of ASCA is determined using yeast cell wall PPM prepared from strain ATCC #38926.

* * * * *

UNITED STATES PATENT AND TRADEMARK OFFICE
CERTIFICATE OF CORRECTION

PATENT NO. : 5,932,429 Page 1 of 2
DATED : August 3, 1999
INVENTOR(S) : Targan et al.

It is certified that error appears in the above-identified patent and that said Letters Patent is hereby corrected as shown below:

Column 4,
Line 24, please delete "absence" and replace therefor with -- absence of --

Column 9,
Line 14, please delete "100-fold ,or" and replace therefor with -- 100-fold, or --

Column 12,
Line 59, please delete "Dnase" and replace therefor with -- DNase --

Column 17,
Line 64, please delete "oups" and replace therefor with -- groups --

Column 18,
Line 1, please delete "did t" and replace therefor with -- did the --
Line 2, please delete "sub oup" and replace therefor with -- subgroup --
Line 3, please delete "in creased" and replace therefor with -- increased --
Line 16, please delete "topica5-ASA" and replace therefor with -- topical 5-ASA --
Line 21, please delete "Crohn 's" and replace therefor with -- Crohn's--
Line 30, please delete "a the" and replace therefor with -- and the --
Line 36, please delete "subgroup PS," and replace therefor with -- subgroup, --
Line 41, please delete "ileocoloni" and replace therefor with -- ileocolonic --
Line 46, please delete "oft e cANCA-" and replace therefor with -- of the cANCA--
Line 54, please delete "e press" and replace therefor with -- express --
Line 55, please delete "relate solely" and replace therefor with -- related solely --

Column 21,
Line 26, please delete "stablished" and replace therefor with -- established --

Column 22,
Line 5, please delete "DNas-positive" and replace therefor with -- DNase-positive --

Column 23,
Line 33, please delete "were grown for two to three days at" and replace therefor with -- were grown for two to three days at --
Line 53, please delete "complexs," and replace therefor with -- complexes, --

UNITED STATES PATENT AND TRADEMARK OFFICE
CERTIFICATE OF CORRECTION

PATENT NO. : 5,932,429
DATED : August 3, 1999
INVENTOR(S) : Targan et al.

It is certified that error appears in the above-identified patent and that said Letters Patent is hereby corrected as shown below:

Column 24,
Line 5, please delete "dissolve in distilled waster," and replace therefor with -- dissolved in distilled water, --

Signed and Sealed this

Thirtieth Day of March, 2004

JON W. DUDAS
*Acting Director of the United States Patent and Trademark Office*